(12) United States Patent
Farnesi et al.

(10) Patent No.: US 7,393,964 B2
(45) Date of Patent: Jul. 1, 2008

(54) PROCESS FOR THE PREPARATION OF NORELGESTROMIN

(75) Inventors: Sara Farnesi, Corciano (PG) (IT); Simone Ferlin, Corciano (PG) (IT)

(73) Assignee: S.N.I.F.F. ITALIA S.p.A., Corciano (PG) (IT)

( * ) Notice: Subject to any disclaimer, the term of this patent is extended or adjusted under 35 U.S.C. 154(b) by 0 days.

(21) Appl. No.: 11/641,954

(22) Filed: Dec. 20, 2006

(65) Prior Publication Data

US 2007/0149812 A1 Jun. 28, 2007

(30) Foreign Application Priority Data

Dec. 22, 2005 (IT) .......................... MI2005A2464

(51) Int. Cl.
*C07J 41/00* (2006.01)

(52) U.S. Cl. ..................................... 552/520

(58) Field of Classification Search .................. 552/520
See application file for complete search history.

(56) References Cited

U.S. PATENT DOCUMENTS

2004/0266741 A1* 12/2004 Tombari et al.

FOREIGN PATENT DOCUMENTS

WO    2005/000868 A1    1/2005

OTHER PUBLICATIONS

NDA 21-180, Ortho Evra, 2001.*

* cited by examiner

*Primary Examiner*—Barbara P Badio
(74) *Attorney, Agent, or Firm*—Nixon & Vanderhye P.C.

(57) ABSTRACT

Process for the preparation of Norelgestromin or 17α-hydroxy-13β-ethyl-18,19-dinorpregn-4-ene-20-yn-3-one oxime, also in crystalline form, in particular with an E/Z isomer ratio of between 1.3 and 1.5.

12 Claims, 12 Drawing Sheets

```
NRTLSP 1976 4400.00 450.00 18.85 93.67 4.00 %T 16 4.00
I
REF 4000 90.69 2000 88.90 600
3902.78 83.56 3801.46 89.22 3749.90 85.74 3290.13 24.70 2932.41 18.85
2871.40 21.57 2358.85 58.02 2341.14 64.61 2103.89 77.30 1716.15 75.49
1698.22 74.29 1636.47 36.04 1540.46 65.70 1448.17 29.40 1432.06 32.88
1363.27 38.06 1338.28 35.07 1281.33 37.45 1228.65 44.05 1178.46 56.06
1163.35 50.56 1129.81 37.20 1110.44 52.83 1048.28 25.83 972.43 27.88
954.13 27.91 881.46 35.14 859.84 28.16 813.98 51.95 752.62 44.49
709.55 38.49 655.23 29.91 505.16 47.44 485.18 53.72
END 34 PEAK(S) FOUND
```

|  | Chemical shift TMS (ppm) |
|---|---|
| C-5 | 157.13-154.92* |
| C-3 | 154.13-150.86* |
| C-4 | 118.06-111.43* |
| C-20 | 87.97 |
| C-17 | 81.39 |
| C-21 | 74.04 |
| C-14 | 50.81 |
| C-9 | 48.84-49.12* |
| C-17 | 47.95 |
| C-8 | 43.0 |
| C-10 | 41.84-41.08* |
| C-16 | 39.46 |
| C-2 | 35.69-35.06* |
| C-6 | 30.98-30.78* |
| C-7 | 28.45 |
| C-12 | 27.25-27.09* |
| C-11 | 26.27-25.76* |
| C-1 | 22.43 |
| C-15 | 20.95 |
| C-18 | 18.85 |
| C-19 | 9.57 |

Fig. 4

| INDEX | FREQUENCY | PPM | HEIGHT | | INDEX | FREQUENCY | PPM | HEIGHT |
|---|---|---|---|---|---|---|---|---|
| 1 | 1451.597 | 7.259 | 276.2 | | 40 | 335.674 | 1.679 | 41.5 |
| 2 | 1450.681 | 7.254 | 92.0 | | 41 | 329.259 | 1.647 | 33.6 |
| 3 | 1308.988 | 6.546 | 52.1 | | 42 | 324.983 | 1.625 | 53.6 |
| 4 | 1174.831 | 5.875 | 73.5 | | 43 | 319.789 | 1.599 | 55.6 |
| 5 | 624.354 | 3.122 | 11.9 | | 44 | 308.487 | 1.543 | 107.2 |
| 6 | 616.245 | 3.082 | 32.3 | | 45 | 305.126 | 1.526 | 140.5 |
| 7 | 614.273 | 3.072 | 20.2 | | 46 | 297.489 | 1.488 | 101.6 |
| 8 | 606.025 | 3.031 | 21.6 | | 47 | 290.759 | 1.454 | 105.9 |
| 9 | 601.443 | 3.008 | 25.9 | | 48 | 281.910 | 1.410 | 53.3 |
| 10 | 517.436 | 2.588 | 385.8 | | 49 | 277.327 | 1.387 | 81.7 |
| 11 | 516.519 | 2.583 | 133.9 | | 50 | 272.440 | 1.362 | 72.5 |
| 12 | 501.245 | 2.507 | 17.1 | | 51 | 267.247 | 1.336 | 64.9 |
| 13 | 488.110 | 2.441 | 45.7 | | 52 | 264.497 | 1.323 | 58.4 |
| 14 | 475.890 | 2.380 | 62.0 | | 53 | 261.442 | 1.307 | 54.6 |
| 15 | 472.530 | 2.363 | 53.1 | | 54 | 254.722 | 1.274 | 50.6 |
| 16 | 463.060 | 2.316 | 45.0 | | 55 | 250.645 | 1.252 | 38.1 |
| 17 | 458.478 | 2.293 | 47.7 | | 56 | 236.087 | 1.181 | 8.6 |
| 18 | 455.118 | 2.276 | 38.5 | | 57 | 225.701 | 1.129 | 20.4 |
| 19 | 449.313 | 2.247 | 61.8 | | 58 | 222.645 | 1.113 | 22.6 |
| 20 | 435.261 | 2.177 | 88.8 | | 59 | 218.482 | 1.068 | 51.9 |
| 21 | 431.595 | 2.158 | 87.8 | | 60 | 205.284 | 1.026 | 182.6 |
| 22 | 420.904 | 2.105 | 102.1 | | 61 | 198.208 | 0.991 | 368.7 |
| 23 | 417.238 | 2.086 | 97.5 | | 62 | 190.571 | 0.953 | 140.8 |
| 24 | 412.045 | 2.060 | 42.5 | | 63 | 178.657 | 0.893 | 13.5 |
| 25 | 406.852 | 2.035 | 78.6 | | 64 | 168.798 | 0.840 | 20.5 |
| 26 | 403.491 | 2.018 | 84.3 | | 65 | 159.717 | 0.799 | 33.8 |
| 27 | 400.436 | 2.002 | 53.6 | | 66 | 156.051 | 0.780 | 29.8 |
| 28 | 394.021 | 1.970 | 59.1 | | 67 | 148.414 | 0.742 | 25.9 |
| 29 | 390.661 | 1.954 | 89.3 | | 68 | 138.028 | 0.690 | 11.5 |
| 30 | 387.606 | 1.938 | 98.7 | | | | | |
| 31 | 380.886 | 1.905 | 52.0 | | | | | |
| 32 | 377.220 | 1.886 | 40.6 | | | | | |
| 33 | 371.416 | 1.857 | 43.7 | | | | | |
| 34 | 367.750 | 1.839 | 44.9 | | | | | |
| 35 | 364.084 | 1.821 | 37.5 | | | | | |
| 36 | 356.142 | 1.781 | 28.4 | | | | | |
| 37 | 353.087 | 1.766 | 30.2 | | | | | |
| 38 | 350.032 | 1.750 | 32.2 | | | | | |
| 39 | 343.006 | 1.715 | 41.0 | | | | | |

| 2Theta | d (A) | Height | Area | FWHM |
|---|---|---|---|---|
| 5.340 | 16.54880 | 643.4 | 8321.2 | 0.3900 |
| 7.761 | 11.39127 | 510.8 | 5860.9 | 0.3600 |
| 8.495 | 10.40829 | 667.6 | 9319.0 | 0.4200 |
| 10.010 | 8.83616 | 625.0 | 9077.4 | 0.4500 |
| 11.733 | 7.54237 | 865.1 | 8352.1 | 0.3000 |
| 12.671 | 6.98595 | 6180.3 | 80226.9 | 0.4200 |
| 13.214 | 6.70016 | 1470.4 | 7334.4 | 0.1500 |
| 13.775 | 6.42836 | 1934.8 | 25053.7 | 0.3900 |
| 14.769 | 5.99777 | 3083.0 | 38755.1 | 0.3900 |
| 15.582 | 5.68681 | 3457.5 | 49593.7 | 0.4500 |
| 16.725 | 5.30043 | 5333.4 | 72777.8 | 0.4200 |
| 17.422 | 5.09014 | 2153.1 | 27988.4 | 0.3900 |
| 18.616 | 4.76625 | 1919.7 | 26491.5 | 0.4200 |
| 20.435 | 4.34585 | 2224.3 | 32573.5 | 0.4500 |
| 21.536 | 4.12603 | 1708.3 | 23879.7 | 0.4200 |
| 22.027 | 4.03516 | 1031.3 | 9060.1 | 0.3000 |
| 23.489 | 3.78728 | 1215.6 | 15473.2 | 0.3900 |
| 24.448 | 3.64077 | 1459.9 | 34411.2 | 0.8100 |
| 24.702 | 3.60402 | 1291.3 | 31212.0 | 0.8100 |
| 25.611 | 3.47808 | 882.2 | 12098.4 | 0.4500 |
| 26.663 | 3.34320 | 520.0 | 8606.3 | 0.5100 |
| 27.567 | 3.23553 | 503.4 | 5842.7 | 0.3900 |
| 28.369 | 3.14592 | 571.3 | 7214.1 | 0.4200 |
| 29.129 | 3.06552 | 428.2 | 5357.2 | 0.3900 |
| 29.816 | 2.99641 | 596.1 | 7731.5 | 0.4200 |
| 31.291 | 2.85847 | 443.3 | 10046.6 | 0.6900 |
| 32.276 | 2.77346 | 494.4 | 6615.0 | 0.4500 |
| 33.261 | 2.69351 | 361.1 | 3844.9 | 0.3600 |
| 34.245 | 2.61836 | 393.1 | 5323.5 | 0.4200 |
| 35.551 | 2.52511 | 497.6 | 6056.9 | 0.4200 |
| 36.052 | 2.49114 | 520.0 | 6757.9 | 0.3900 |
| 37.937 | 2.37161 | 404.2 | 5323.5 | 0.4200 |
| 40.430 | 2.23095 | 412.1 | 5433.3 | 0.4200 |
| 41.149 | 2.19361 | 400.1 | 4800.0 | 0.3600 |
| 41.786 | 2.16161 | 359.3 | 4072.8 | 0.3900 |
| 44.681 | 2.02807 | 308.5 | 3550.0 | 0.3600 |

US 7,393,964 B2

PROCESS FOR THE PREPARATION OF NORELGESTROMIN

OBJECT OF THE INVENTION

The present invention relates to a process for the preparation of Norelgestromin or 17α-hydroxy-13β-ethyl-18,19-dinorpregn-4-ene-20-yn-3-one oxime, also in crystalline form. The invention also relates to Norelgestromin, in particular with an E/Z isomer ratio of between 1.3 and 1.5, obtainable with the aforesaid process.

PRIOR ART

As it is known, norelgestromin is a progestin compound that has been widely utilized since a long time, for example, in female hormone replacement therapy and also, in association with suitable estrogen compounds, such as ethinyleoestradiol, as inhibitor of female ovulation, i.e. as an oral contraceptive. Associations between norelgestromin and at least one estrogen compound are also used, for example, to treat changes in the cervical mucous membrane and endometrium.

The widespread use of norelgestromin both as oral contraceptive in association with estrogens and alone in hormone replacement therapy, has meant that processes for its preparation have been studied for long. Besides supplying the product with high levels of purity, these processes must also be advantageous from a synthetic point of view and thus relatively simple to be carried out on an industrial scale.

According to the most widely used process, starting from Levonorgestrel or 17α-hydroxy-13β-ethyl-18,19-dinorpregn-4-ene-20-yn-3-one, a protection reaction of the hydroxyl group in position 17 is performed, e.g. an acetylation reaction, then the function group in position 3 is transformed into oxime obtaining a 17 acetoxy derivative, and subsequently the acetoxy group in position 17 is hydrolyzed, to restore the initial hydroxyl group. This process, which is described, for example, in WO 2005/000868, allows the desired norelgestromin product to be obtained with a high level of purity, but has the considerable disadvantage of requiring to carry out a protection reaction of the hydroxyl group in position 17 first, and a subsequent removal reaction of said group, after the oxime, which characterizes the norelgestromin and distinguishes it from the initial product Levonorgestrel has formed. In fact, from the point of view of process costs, the protection/deprotection reactions involve a considerable expenditure, also in relation to the decreased yield of the final product.

Moreover, criteria for approval of norelgestromin have recently been established wherein the ratio between the E isomer and the Z isomer thereof are strictly regulated. According to these criteria, established for example by the Food and Drug Administration (FDA) in the USA (FDA, Center for drug valuation and research application, n.21-180, Chemistry review) the ratio between E isomer and Z isomer must be between 1.3 and 1.5.

Consequently, there is an evident need to implement synthesis processes of norelgestromin, which on the one hand reduce the number of steps and are therefore more advantageous from the point of view of cost and guarantee high yields, and on the other make it possible to obtain an E/Z isomer ratio within the limits established by internationally recognized criteria for norelgestromin.

US 2004/0266741 describes a process for the preparation of norelgestromin starting from levonorgestrel which provides for:

a) producing hydroxylamine acetate in situ,
b) adding levonorgestrel and forming the oxime,
c) adding an acid;
d) adding a base.

This process provides for formation of the oxime, starting from levonorgestrel, in an alcohol medium, preferably methanol or isopropanol, by heating the resulting suspension to a temperature between 40° and the reflux temperature of the solvent, i.e. approximately 65-80° C. At the end of the reaction, the suspension is treated with acids and, after a certain time, treated with an organic base, filtered and the crude reaction product is precipitated from water. Once obtained, the crude product is recrystallized from aprotic polar solvent or mixtures of aprotic polar solvents, in particular from acetonitrile. The crude product, obtained by precipitation from water, is characterized by an E/Z ratio of approximately 1.3, while once crystallized from aprotic polar solvent or mixtures of solvents, it is characterized by an E/Z ratio of 1.4.

Although it avoids the protection/deprotection of the hydroxyl group in position 17, this process still has several disadvantages: it is laborious, requires the crude product to be obtained from an aqueous medium and entails a series of steps that do not contribute towards improving the general process cost from an industrial point of view.

OBJECTS OF THE INVENTION

The object of the present invention is to provide a process for the preparation of norelgestromin which is advantageous from a point of view of cost, which makes it possible to obtain the product with high yields and which entails a limited number of steps.

A further object of the present invention is to provide a process for the preparation of norelgestromin characterized by an E/Z isomer ratio between 1.3 and 1.5.

Yet another object of the present invention is to provide a process for the preparation of norelgestromin which makes it possible to obtain a product in crystalline form.

One more object of the present invention is to provide norelgestromin characterized by an E/Z ratio of between 1.3 and 1.5 and by high purity, obtainable through an advantageous process from the point of view of cost and which consists of only a few steps.

BRIEF DESCRIPTION OF THE DRAWINGS

The invention is further illustrated with respect to the attached drawings in which

FIG. 4 shows the table concerning the distribution of the signals of the spectrum in FIG. 3, again in relation to the numbering as given in FIG. 2;

Figure 9:
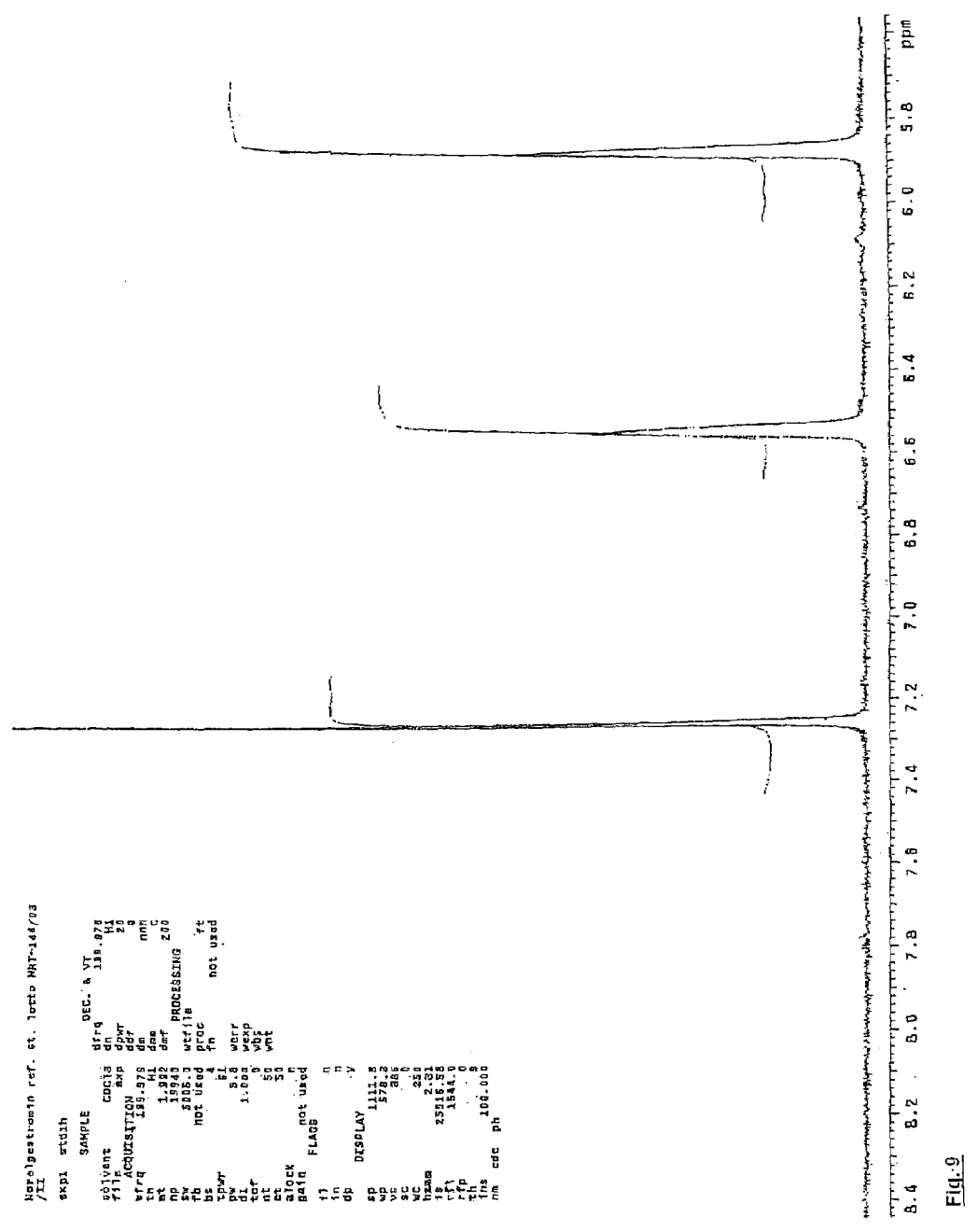

FIGS. 6 to 10 show the proton NMR spectra performed on Norelgestromin in order to determine the E/Z isomer ratio;

FIG. 6 shows the proton spectrum of Norelgestromin obtained according to the process object of the present invention;

FIG. 7 gives the details of the signals recorded;

FIG. 8 shows part of the spectrum of FIG. 6 amplified;

FIG. 9, FIG. 10 shows the proton spectrum of norelgestromin in $CDCl_3$ with the addition of $D_2O$;

DESCRIPTION OF THE INVENTION

Figure 1:
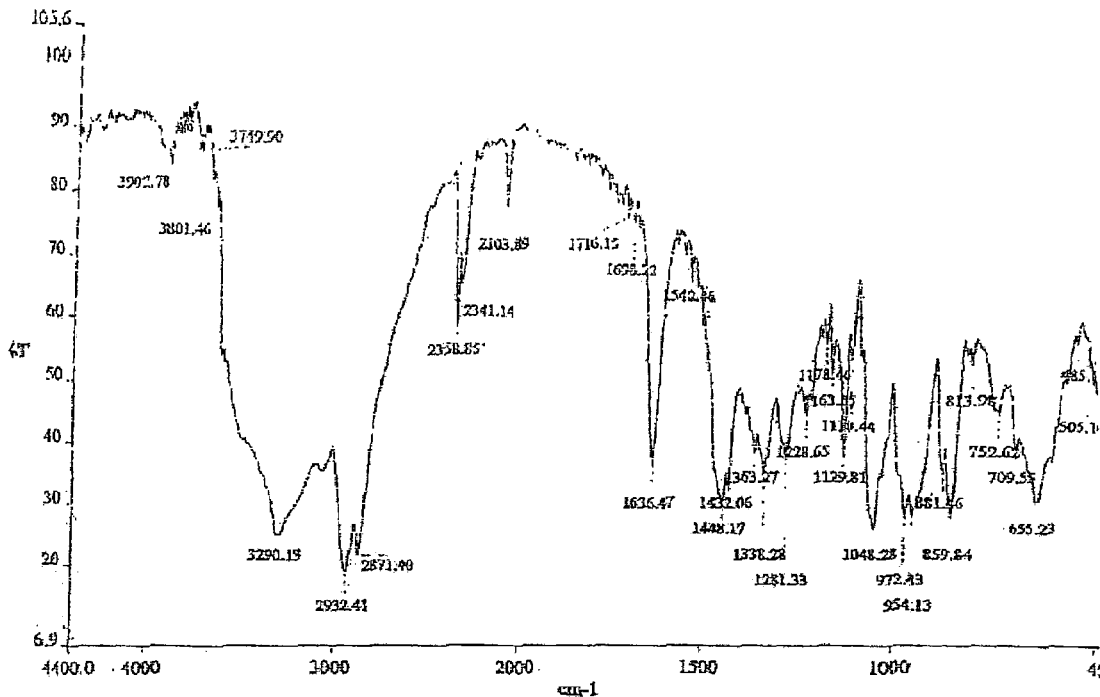
FIG. 1 shows the IR spectrum, produced as described in example 4, of norelgestromin obtained according to the process forming the object of the present invention.

These and other objects and relative advantages, which will be better specified in the description hereunder, are obtained by a process for the preparation of norelgestromin comprising:
a) the reaction of levonorgestrel with an hydroxylamine salt, obtaining the corresponding oxime
b) acidification of the solution/suspension thus obtained to obtain crude norelgestromin
c) optional subsequent purification of said crude norelgestromin, characterized in that said reaction of levonorgestrel according to step a) is produced in at least one non protic or aprotic polar solvent and said step b) is produced by adding an organic solvent non miscible with water.

Non protic or aprotic polar solvent is intended as a solvent which cannot behave as a hydrogen bond donor, i.e. a solvent that does not have —OH groups.

In particular, said step a) is produced in pyridine by direct reaction with hydroxylamine hydrochloride.

Moreover, again according to the present invention, said purification step c) of the final crude norelgestromin product is advantageously performed by crystallization of the crude product from ethanol, ethanol/water.

The process according to the present invention has numerous advantages as compared to prior art processes. In the first place, it makes it possible to perform the reaction to form the oxime, i.e. to treat levonorgestrel with a hydroxylamine salt, in particular hydroxylamine hydrochloride, without having to perform any protection/deprotection reaction of the hydroxyl group in position 17, as is instead required in the majority of prior art processes for the preparation of norelgestromin. Moreover, it has further advantages, which will be illustrated hereunder.

According to the invention, the reaction between levonorgestrel and hydroxylamine hydrochloride is performed in at least one non protic polar solvent, e. g. pyridine, or also advantageously in a mixture of non protic polar solvents, such as in a mixture of pyridine and acetonitrile. In both cases, it has surprisingly been found that the hydroxylamine hydrochloride and the initial levonorgestrel react at temperatures ranging from 5 to 30-35° C., in particular at room temperature, i.e. at a temperature of approximately 20-25° C. Therefore, the reaction takes place with high yields and in times in a period of time of about few hours, with the enormous advantage that it can be carried out at room temperature, i.e. without the need to perform heating or forced cooling of the reaction mixture. Being able to perform a reaction at room temperature is an enormous advantage, as it simplifies the process significantly, makes it possible to use less elaborate and simpler equipment, consequently representing a considerable advantage as regards cost, also in terms of energy saving, from the point of view of process industrialization. Moreover, the reaction provides comparable results in a temperature range of 5 to 35° C., meaning that even small corrections to the process temperature will not be required either in summer or winter, merely leaving it to react at room temperature, which can also be lower in winter than the room temperature value of the summer. In substance, stating that the reaction takes place at room temperature does not mean it must necessarily take place at 25° C., but means that no corrections to the temperature value are required, with the consequent advantages already mentioned above.

The choice of solvent or mixture of solvents utilized in this first step of the process according to the present invention, is therefore not random, as it has been seen, that the use of pyridine or of a pyridine/acetonitrile mixture makes it possible to perform the transformation of levonorgestrel into the corresponding oxime without it being necessary to heat the reaction mixture. Instead, if the process described in US 2004/0266741 is utilized, the reaction described between hydroxylamine acetate and levonorgestrel, performed in methanol or isopropanol, which are protic polar solvents, i.e. provided with functional —OH groups and therefore capable of acting as hydrogen bond donor, must take place at a temperature of between 40° C. and 65-80° C., i.e. between 40° C. and the boiling temperature of the solvent used. The process described in US 2004/0266741 therefore requires heating of the reaction mixture, with consequent disadvantages, also in relation to the process costs, above all from an industrial point of view.

According to the present invention, once the reaction of levonorgestrel has terminated to give the corresponding oxime, the reaction mixture is treated with water, acids and an organic solvent non miscible with water, for example methylene chloride. This reaction step also has considerable advantages as compared to those described in the prior art. The first advantage is that having performed the previous step at room temperature, no cooling of the reaction mixture is required before treatment with acids, but the mixture is treated directly with water and hydrochloric acid, in particular hydrochloric acid at 35%. Not having to cool the reaction mixture before treatment with acids has considerable advantages both from the point of view of energy and from the point of view of simplification of the equipment utilized. Moreover, treatment of the reaction mixture with organic solvent non miscible with water, in particular with methylene chloride, makes it possible to obtain a system with two phases, in particular an aqueous phase and an organic phase immiscible with each other. All the salts, all the compounds soluble in water and any impurities present in the mixture will be dissolved in the aqueous phase, while the final product norelgestromin will be dissolved in the organic phase. Separation of the two phases will therefore make it possible to separate the norelgestromin from the salts and from the other impurities present and, by concentration of the solvent, it will therefore be possible to directly obtain the product with high levels of purity and high yields.

The process according to the present invention therefore offers a further advantage as compared to the one described in US 2004/0266741, In fact, after the reaction step between levonorgestrel and hydroxylamine acetate, the process according to US 2004/0266741 provides for a cooling step of the reaction mixture, followed by the addition of concentrated hydrochloric acid thereto and, subsequently, by the addition of a base to the mixture. The mixture obtained according to US 2004/0266741 is a mixture in water, from which the salts are precipitated and must therefore be filtered, with high risk of decreasing yields in the desired product, and in which the desired crude product remains. Therefore, the norelgestromin according to the aforesaid prior art document is obtained in water and must be precipitated therefrom, with evident disadvantages, especially from an industrial point of view, also bearing in mind the problems related to the disposal of waste waters. The process according to the present invention does not require the step relative to treatment with bases of the solution previously treated with acids and therefore offers a considerable advantage as compared to the process according to prior art, as a step (the treatment with bases) can be omitted and moreover the desired product can be obtained in organic solvent, while the salts and impurities remain in the aqueous phase and can thus be easily removed.

A further characteristic advantageous step of the process according to the present invention is the one relative to the treatment of the crude norelgestromin to obtain a product with an E/Z isomer ratio of between 1.3 and 1.5, as established by current international criteria. Using the process according to the present invention crude norelgestromin with a variable E/Z isomer ratio of between 1.6 and 2.0 is obtained. If a final product characterized by a lower E/Z isomer ratio is required, in particular between 1.3 and 1.5, it is therefore necessary to perform at least one purification treatment. Surprisingly, it was found that ethanol purification of norelgestromin obtained through the process according to the present invention makes it possible to obtain a crystalline product with high purity and characterized by an isomer ratio reduced to E/Z 1.4 and in any case within the 1.3-1.5 range. In fact, also in this case the choice of solvent is not random, as the ratio between the E and Z isomers changes significantly according to the choice of purification solvent. Moreover, US 2004/0266741 reports obtaining crude norelgestromin with an E/Z isomer ratio of 1.31, In this case, the crude product is purified by acetonitrile, obtaining a final product characterized by an increased E/Z ratio as compared to the crude product prior to purification. The process according to the present invention leads to the formation of crude norelgestromin characterized by an E/Z ratio much higher than the one that characterizes crude norelgestromin obtained according to US 2004/0266741, also due to the operating differences characterizing the two processes. The purification solvent employed as described according to prior art would take the crude product obtained with the process according to the present invention to a final product characterized by an even higher E/Z isomer ratio and consequently even further from the range currently considered optimal. Therefore, starting from the crude norelgestromin obtained according to the process of the present invention, a suitable solvent must be utilized, and ethanol has thus been identified as the preferred purification solvent.

The use of ethanol according to the finding also has a further advantage, represented by the fact that the norelgestromin thus obtained is in crystalline form. Obtaining a crystalline product has a series of advantages, such as facilitating conditions for preservation of the isolated product, increased manageability of the product when it requires to be optionally formulated in association with other active substances or with excipients of various type, and increased solubility. It has in fact been found that if the crude reaction product is treated with, for example, acetonitrile, the product obtained is not in crystalline form, but in an amorphous form. In this case, it is much more difficult to treat, preserve and optionally formulate with other active substances or additives of various type, besides being much more difficult to dissolve in a suitable solvent.

Therefore, the choice of solvent according to the present invention is not random, but guided by the need to satisfy several conditions: on the one hand the need to lower the ratio between the E isomer and the Z isomer in relation to the ratio obtained at the end of the reaction, i.e. in relation to the ratio of the crude product, and on the other the need to obtain an improved product as compared to the one obtained with prior art processes, namely the need to obtain a crystalline product, which facilitates treatments as compared to the same product in amorphous form.

According to the present invention, a solvent, or mixtures of said solvent, has therefore surprisingly been found, to use in the reaction step between levonorgestrel and hydroxylamine, which makes it possible to carry out the reaction at room temperature and to avoid a step as compared to the prior art description. In fact, the use of pyridine or its mixtures thereof, according to the invention, makes it possible to avoid heating of the reaction mixture, as well as subsequent cooling thereof prior to adding the acid and the subsequent addition of a base. Similarly, the choice of purification solvent, and in the case of the present invention, the use of ethanol, allows the E/Z isomer ratio of the crude product to be taken to the value currently required at international level and also makes it possible to obtain a product in crystalline form.

Moreover, any currently accepted maximum residual quantity of ethanol in the final product is much higher than the corresponding quantity of acetonitrile.

Figure 2:
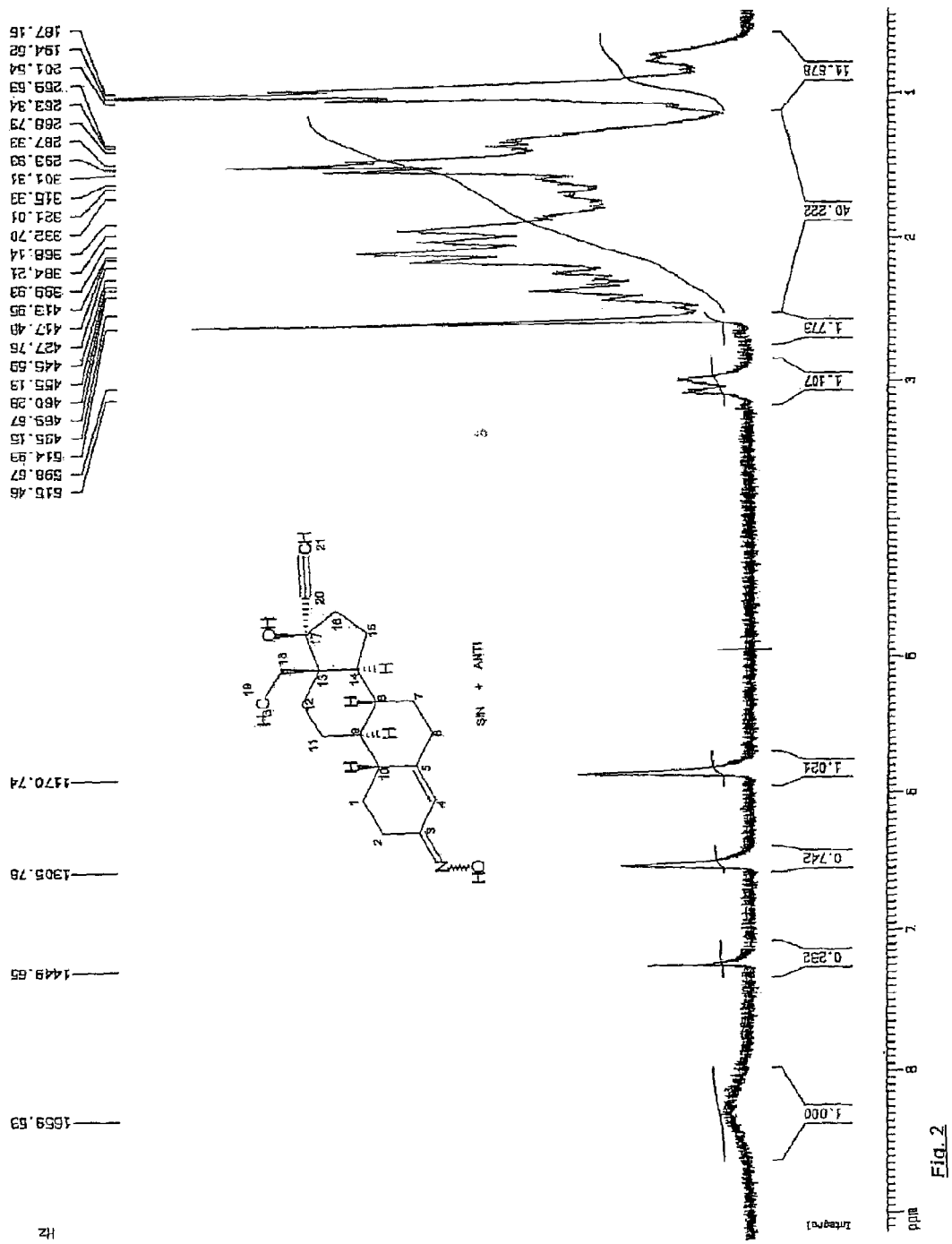
FIG. 2 shows the proton magnetic resonance spectrum of Norelgestromin and gives the numbering of the molecule as utilized to assign signals.
Figure 5:
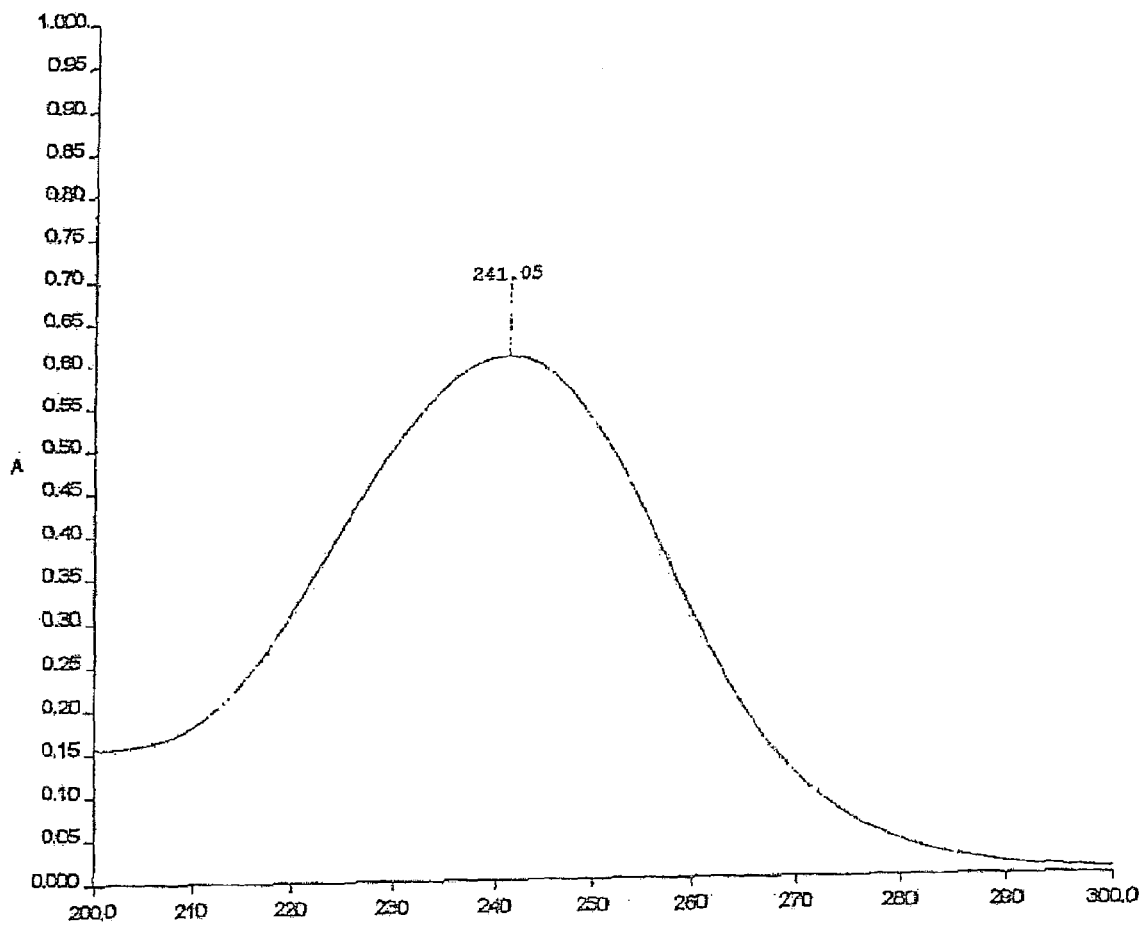
FIG. 5 shows the UV spectrum of norelgestromin.
Figure 6:
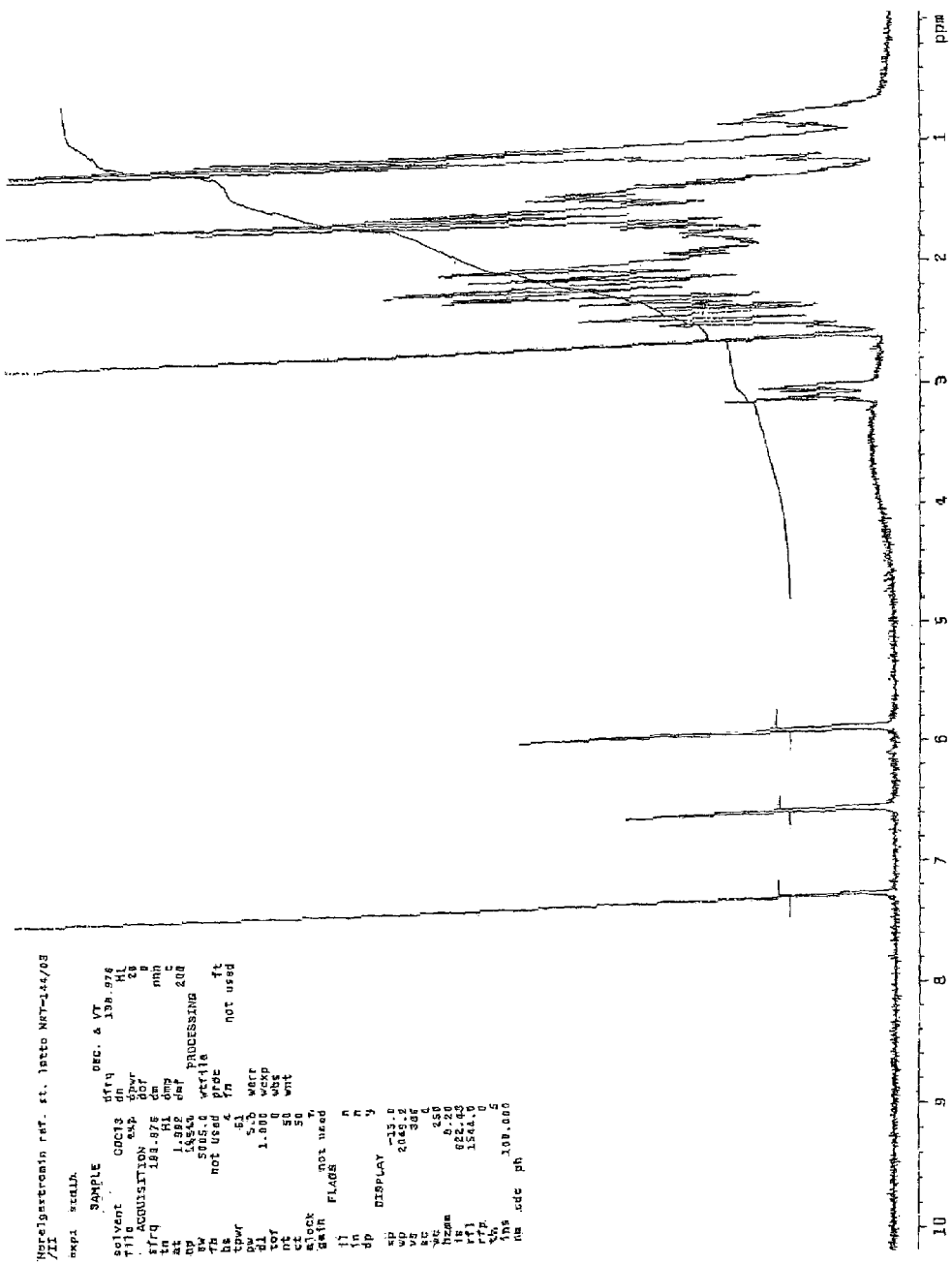
Figure 8:
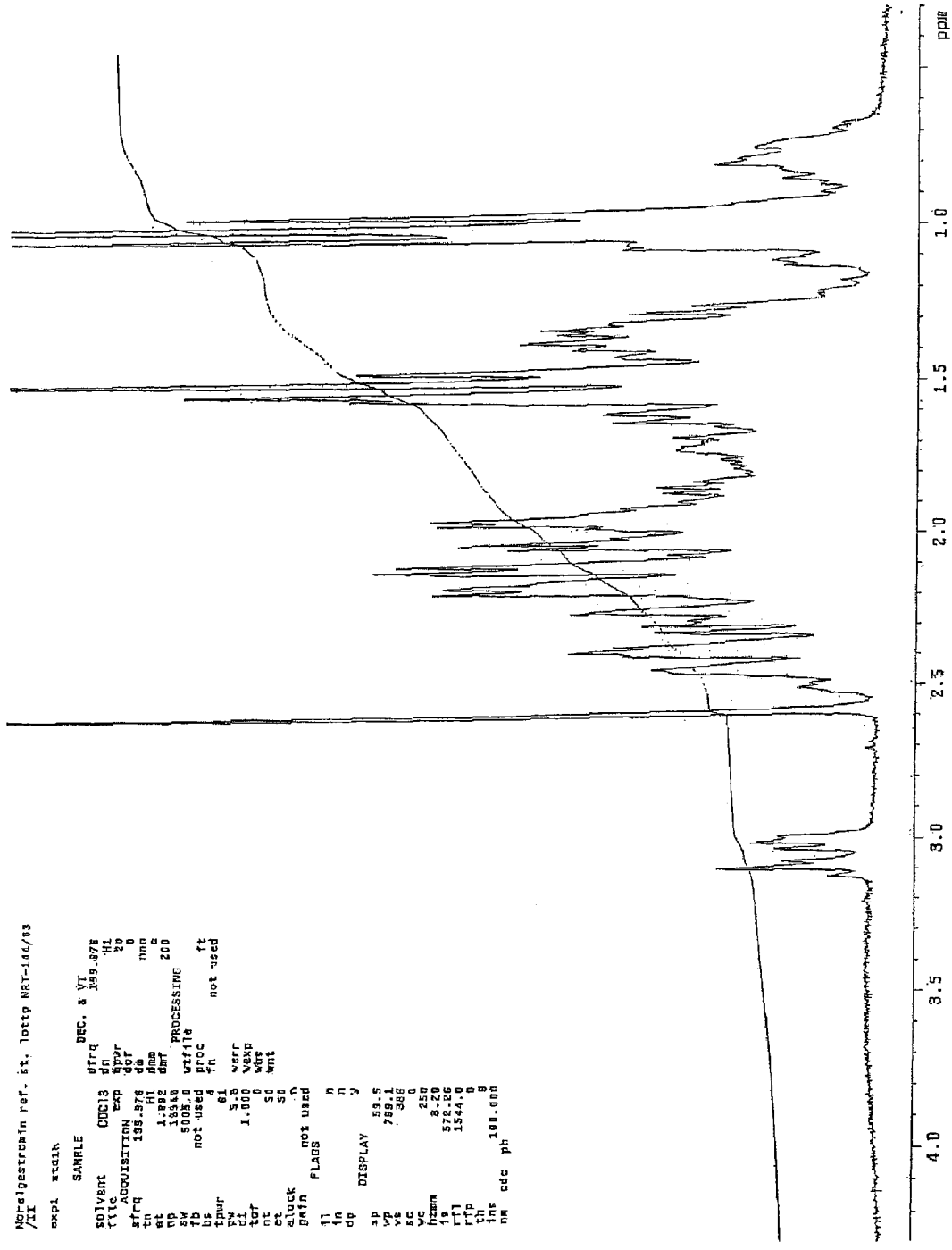
Figure 10:
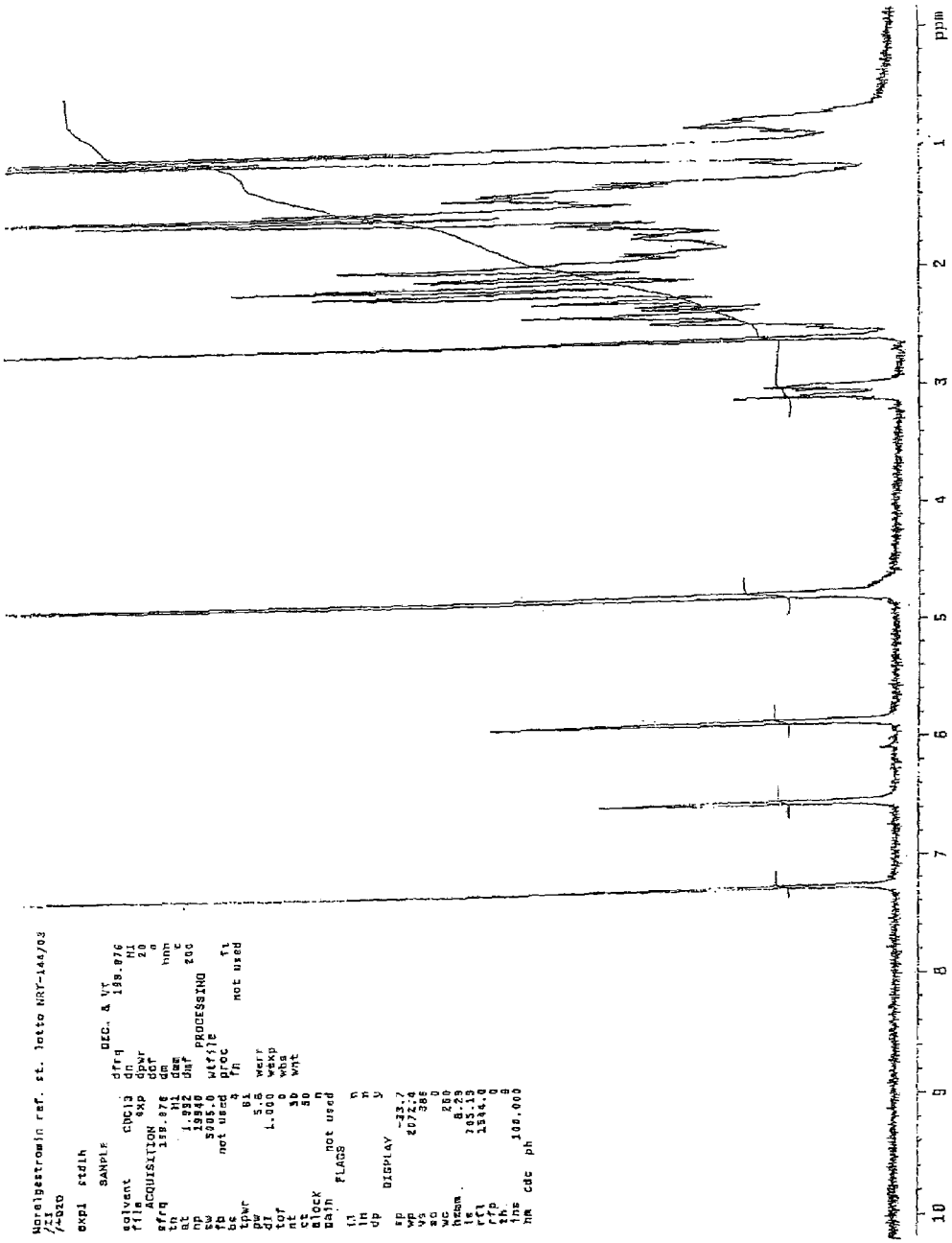
Figure 11:
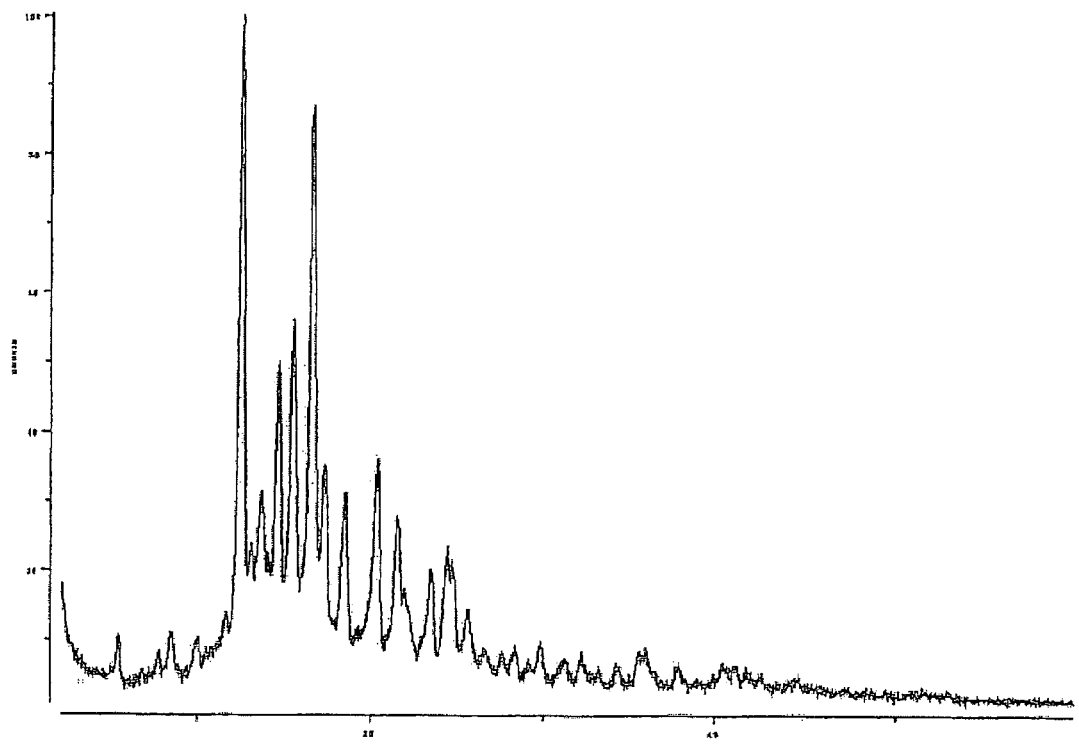
FIG. 11 shows the XRPD spectrum of the crystalline product, obtained according to the process of the present invention, and in particular by crystallization of the crude product from ethanol.
Figure 12:
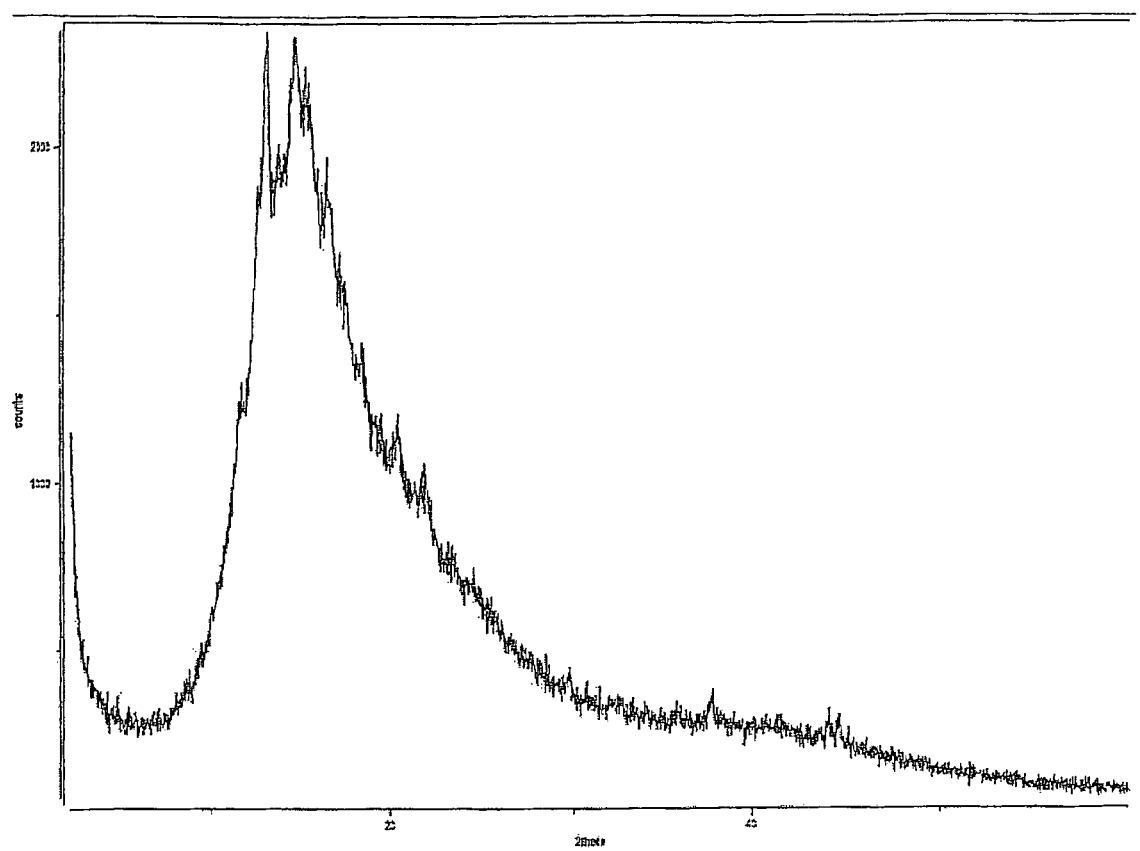
FIG. 12 shows the same spectrum performed on the product obtained by purification from acetonitrile.

The description above will be more clearly indicated with the aid of the practical examples of embodiments below, provided purely by way of a non-limiting indication of the present invention. In addition to the examples provided below, the following figures are also attached, for better comprehension and characterization of the norelgestromin reaction product. In particular, FIG. 1 shows the IR spectrum, produced as described in example 4, of norelgestromin obtained according to the process forming the object of the present invention; FIG. 2 shows the proton magnetic resonance spectrum of Norelgestromin and gives the numbering of the molecule as utilized to assign signals; FIG. 3 shows the $^{13}$C-NMR spectrum of Norelgestromin, while FIG. 4 shows the table concerning the distribution of the signals of the spectrum in FIG. 3, again in relation to the numbering as given in FIG. 2. FIG. 5 shows the UV spectrum of norelgestromin, while FIGS. 6 to 10 show the proton NMR spectra performed on Norelgestromin in order to determine the E/Z isomer ratio. In particular, FIG. 6 shows the proton spectrum of Norelgestromin obtained according to the process object of the present invention; FIG. 7 gives the details of the signals recorded; FIG. 8 shows part of the spectrum of FIG. 6 amplified as well as FIG. 9, FIG. 10 shows the proton spectrum of norelgestromin in CDCl$_3$ with the addition of D$_2$O. FIG. 11 shows the XRPD spectrum of the crystalline product, obtained according to the process of the present invention, and in particular by crystallization of the crude product from ethanol, while FIG. 12 shows the same spectrum performed on the product obtained by purification from acetonitrile.

EXAMPLE 1

| Synthesis of Norelgestromin on industrial scale | |
|---|---|
| Acetonitrile | kg 45.7 |
| Pyridine | kg 12.2 |
| Levonorgestrel | kg 9.3 |
| Hydroxylamine hydrochloride | kg 2.79 |
| Hydrochloric acid 35% | kg 45.5 |
| Methylene chloride | kg 245.8 |
| Water | kg 329.2 |
| n-hexane | kg 33.8 |

Acetonitrile, pyridine, levonorgestrel and hydroxylamine hydrochloride are charged in a reactor. The mixture is made to react under stirring at room temperature. After 1 hour a first TLC (Thin Liquid Chromatography) check is performed and subsequently the reaction is checked every 30 minutes until complete disappearance of the initial levonorgestrel. The reaction mixture is then transferred to a second reactor containing potable water, hydrochloric acid at 35% and methylene chloride, and is left to react under stirring for approximately 20 minutes. After this time, stirring is interrupted and the two phases are left to separate for approximately 20 minutes. The organic phase is separated and concentrated under vacuum until the residual volume is 30 l, then left to cool to room temperature. At this point n-hexane is added slowly (in approximately 30 minutes), the mixture is cooled to between 0 and 5° C. and kept under stirring for at least 2 hours. The solid mass obtained is filtered through a Buckner filter and washed with cold n-hexane (between 0 and 5° C.). The crude norelgestromin thus obtained is dried under vacuum at a temperature of 40±5° C., obtaining 8.0 kg of crude product.

EXAMPLE 2

| Purification of Norelgestromin | |
|---|---|
| Crude norelgestromin (dry) | kg 8.0 |
| Absolute ethanol | kg 53.0 |
| Purified water | kg 162.6 |

Absolute ethanol and crude norelgestromin are charged in a reactor, left under stirring at room temperature for approximately 30 minutes (in order to obtain a solution). The solution is filtered and transferred to another reactor, then purified water is added slowly (in approximately 1 hour and 30 minutes), keeping the reaction under stirring and at room temperature for at least two hours. The precipitate is filtered through a Buckner filter and washed with purified water, then left to dry under vacuum at a temperature of 40±5° C., until the water content (determined with the Karl Fischer method) is less than 1%. The yield of pure and dry Norelgestromin is 6.5 kg.

As can be noted from the examples given above and again according to the present invention, the ratio between reaction solvent and levonorgestrel is approximately 6:1, while the molar ratio between hydroxylamine hydrochloride and levonorgestrel is approximately 1.35-1.4, In the acidification step of the reaction mixture, subsequent to the reaction between levonorgestrel and hydroxylamine, the molar ratio between acid and initial levonorgestrel is approximately 4.

The yield of crude norelgestromin is approximately 86% while the yield of product after purification is approximately 81%. The final product has a titer of approximately 99%.

EXAMPLE 3

Characterization of Pure Norelgestromin Obtained as Described in Examples 1 and 2

| ANALYSIS | u. meas. | LIMITS Min. | Max. | RESULTS |
|---|---|---|---|---|
| Appearance | Crystalline white powder | | | conforming |
| Identification | Corresponds to the standard | | | conforming |
| (IR, HPLC) | | | | |
| Titer | % | 98.0 | 102.0 | 99.3 |
| Correlated substances | | | | |
| (HPLC): | % | — | 0.3 | 0.07 |
| Levonorgestrel | % | — | 0.3 | not detect. |
| Unknown single | % | — | 1.0 | 0.07 |
| total | | | | |
| E/Z Norelgestromin ratio (NMR) | | 1.3 | 1.5 | 1.4 |
| Water content (KF) | | | | 0.6% |
| Sulphated Ash | % | | 0.5 | <0.1 |
| Residual solvents - acetonitrile | ppm | | 410 | 309 |
| Storage | Store in watertight and light-proof containers | | | |

EXAMPLE 4

IR Analysis of Norelgestromin

The infrared spectrum, given in FIG. 1, was recorded with a Perkin Elmer Spectrum RX FT/IR spectrometer. The Norelgestromin spectrum was obtained from a dispersion in potassium bromide. Interpretation of the main absorption bands is given in the following schedule:

| IR absorption band cm$^{-1}$ | Assignment |
|---|---|
| 3400-3500 | —OH |
| 3290.13 | —CC—H |
| 2103.89 | Triple bond C—C |
| 1636.47 | —C=N—OH |

EXAMPLE 5

5.1 $^1$H-NMR Analysis of Norelgestromin

The proton magnetic resonance spectrum of Norelgestromin was obtained utilizing a Brucker AC 200 instrument. The sample of Norelgestromin was analyzed in a solution of CDCl$_3$ at 200 MHz.

Interpretation of the spectrum is given in the following table, with reference to the numbering of the molecule as indicated in FIG. 2; the spectrum as obtained is also indicated in FIG. 2:

| Proton position multiplicity | chemical shift TMS (ppm) |
|---|---|
| 20 t(1H) | 0.90 |
| 21 s(1H) | 2.50 |
| 2 m(2H) | 3.0 |
| 4(E) s(1H) | 5.80 |
| 4(Z) s(1H) | 6.50 |
| OH s(1H) | 8.30 |

5.2 $^{13}$C-NMR Analysis of Norelgestromin

Figure 3:
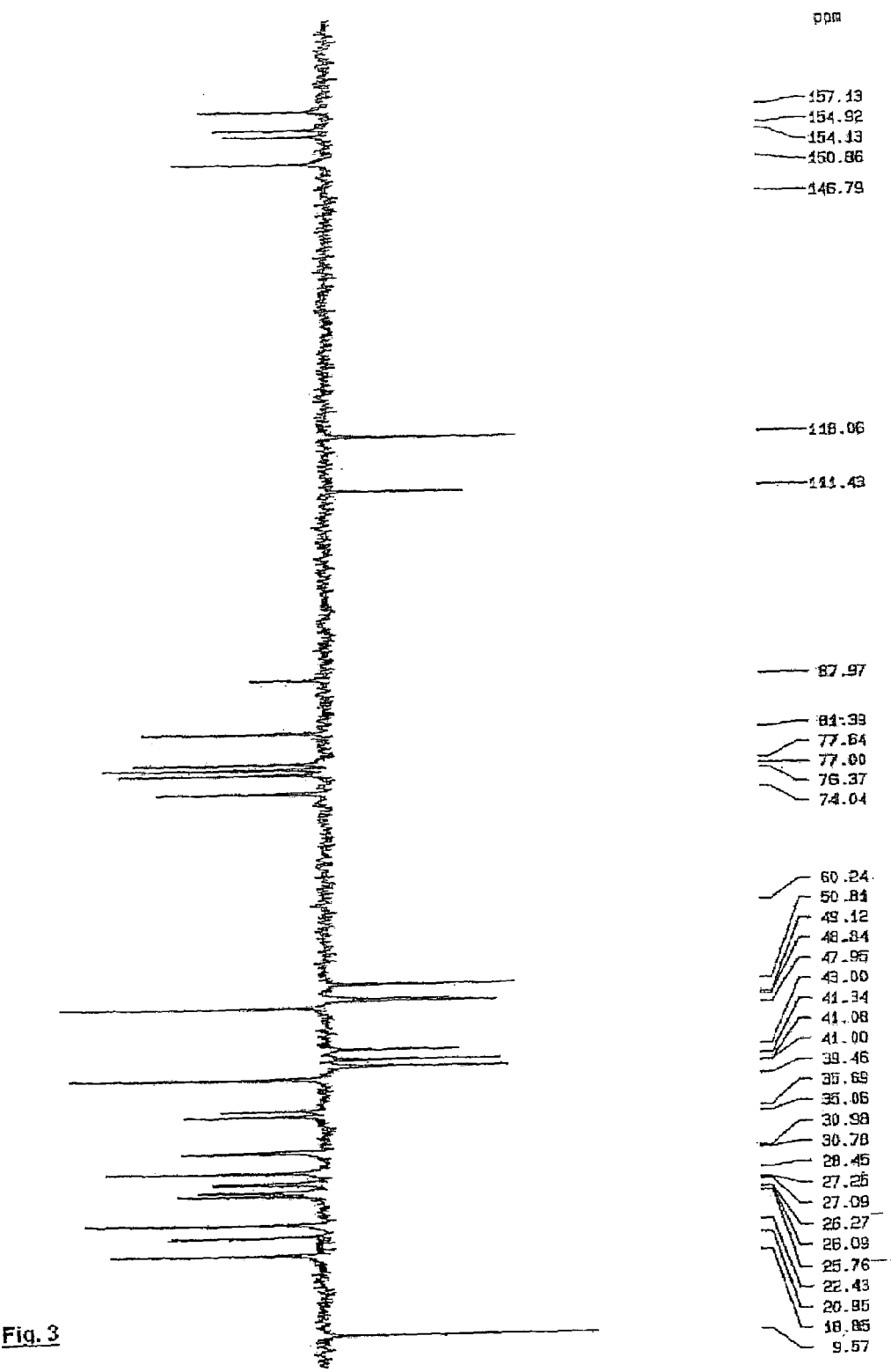
FIG. 3 shows the $^{13}$C-NMR spectrum of Norelgestromin.

The $^{13}$C-NMR spectrum of Norelgestromin, obtained in CDCl$_3$ and recorded on a Brucker AC 200 NMR spectrophotometer at 50.32 MHz, is given in FIG. 3, while FIG. 4 shows a table with assignment of the various signals. In this table, the asterisk indicates the different chemical shifts of the two isomers. The reference numbering of the molecule is again the same as that in FIG. 2.

EXAMPLE 6

UV Analysis of Norelgestromin

The ultraviolet absorption spectrum of Norelgestromin was performed utilizing a Perkin Elmer UV/VIS Lambda 20 spectrophotometer. The sample was analyzed in ethanol and the graph relative to the analysis is given in FIG. 5. The spectrum has a maximum absorption at λ=241.05 nm.

EXAMPLE 7

Elementary Analysis of Norelgestromin

The elementary analysis of Norelgestromin was obtained using a Carlo Erba Analyzer 1106 CHNS/O instrument. The values calculated for $C_{21}H_{29}NO_2$, molecular weight 327.5 are as follows: C 77.02%, H 8.93%, N 4.28%, while the values found are as follows: C 77.01%, H 9.16%, N 4.26%.

EXAMPLE 8

NMR Study for Calculation of the E/Z Isomer Ratio of Norelgestromin

The 1H-NMR analysis of Norelgestromin to determine the E/Z isomer ratio was performed at the following conditions using a Varian Geminy 200 instrument operating at 200 MHz in solvent CDCl$_3$ and CDCl$_3$+D$_2$O. Analysis of the $^1$H-NMR spectrum shows that the hydrogen in position 4 has a different chemical shift in the two different isomers E (anti) and Z (syn). In fact, the signal relative to the hydrogen atom in position 4 in the E (anti) isomer is at 5.88 ppm, while in the Z (syn) isomer it is at 6.55 ppm. From measuring the areas underlying the two hydrogen peaks in position 4, it can be calculated that the E/Z isomer ratio is 1.4.

EXAMPLE 9

XRD Analysis

Each sample was analyzed through X ray powder diffraction with a Philips X'PERT APD diffractometer, CuKalfa radiation (lambda=1.54184 Å) monochromatized on the diffracted ray with curved graphite monochromator, utilizing divergence and antidivergence slits of 1° and receiving slit of 0.2 mm. In order to minimize the background, the samples were placed on a quartz single crystal sample holder cut so that it does not produce reflections in the diffraction field used.

Visual analysis showed that the sample had a homogeneous grain size, with sub-millimeter sized dimensions. Therefore, these samples were placed on the sample holder as they were, without further grinding or the like.

Acquisition was performed through the step scanning process using the following parameters: scanning step 0.03° 2theta; scanning time 1 s per step; scanning range 2-60° 2theta. The spectral patterns relative to the samples analyzed are given in FIGS. 11 and 12. In particular, the spectrum of FIG. 11 refers to a sample of norelgestromin crystallized according to the description in example 2, using ethanol and therefore obtaining a crystalline product, as shown by the analysis given. The spectrum in FIG. 12 instead refers to a sample of norelgestromin obtained as described in example 1, but purified by subsequent treatment with acetonitrile, to obtain an amorphous product, in place of a crystalline product, as it is instead obtained when the crude product is treated with ethanol in the final purification step.

The invention claimed is:

1. Process for the preparation of norelgestromin comprising:
   a) the reaction of levonorgestrel with a hydroxylamine salt, obtaining the corresponding oxime
   b) acidification of the solution/suspension thus obtained to obtain crude norelgestromin
   c) optional subsequent purification of said crude norelgestromin wherein said reaction of levonorgestrel according to step a) is carried out in at least one non protic or aprotic polar solvent and said step b) is carried out by adding an organic solvent non miscible with water.

2. Process as claimed in claim 1, wherein said non protic or aprotic solvent is pyridine.

3. Process as claimed in claim 1, wherein said non protic or aprotic polar solvent is a mixture of pyridine and at least one other non protic or aprotic polar solvent.

4. Process as claimed in claim 3, wherein said other non protic polar solvent is acetonitrile.

5. Process as claimed in claim 1, wherein said purification step c) is carried out in ethanol or ethanol/water.

6. Process as claimed in claim 5, wherein said purification step is carried out in ethanol thus obtaining norelgestromin in crystalline form.

7. Process as claimed in claim 1, wherein said hydroxylamine salt is hydroxylamine hydrochloride.

8. Process as claimed in claim 1, wherein said step a) is carried out at temperatures ranging from 5 to 35° C.

9. Process as claimed in claim 8, wherein said step a) is carried out at a temperature of about 20-25° C.

10. Process as claimed in claim 1, wherein said non protic or aprotic polar solvent and levonorgestrel are in a ratio of 6:1.

11. Process as claimed in claim 1, wherein the molar ratio between said hydroxylamine salt and levonorgestrel is between 1.3 and 1.4.

12. Process as claimed in claim 1, wherein the molar ratio between acid used in step b) and levonorgestrel is 4.

* * * * *